(12) United States Patent
Hancock

(10) Patent No.: US 12,290,311 B2
(45) Date of Patent: May 6, 2025

(54) MICROWAVE AMPLIFICATION APPARATUS FOR AN ELECTROSURGICAL INSTRUMENT

(71) Applicant: CREO MEDICAL LIMITED, Chepstow (GB)

(72) Inventor: Christopher Hancock, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 839 days.

(21) Appl. No.: 17/604,315

(22) PCT Filed: Apr. 28, 2020

(86) PCT No.: PCT/EP2020/061764
§ 371 (c)(1),
(2) Date: Oct. 15, 2021

(87) PCT Pub. No.: WO2020/221751
PCT Pub. Date: Nov. 5, 2020

(65) Prior Publication Data
US 2022/0241011 A1    Aug. 4, 2022

(30) Foreign Application Priority Data
Apr. 30, 2019    (GB) .................................... 1906010

(51) Int. Cl.
*A61B 18/18*    (2006.01)
*H02M 3/155*    (2006.01)
(Continued)

(52) U.S. Cl.
CPC ......... *A61B 18/1815* (2013.01); *H02M 3/155* (2013.01); *H03F 3/21* (2013.01);
(Continued)

(58) Field of Classification Search
CPC ...... A61B 18/1815; A61B 2018/00577; A61B 2018/00589; A61B 2018/00601;
(Continued)

(56) References Cited

U.S. PATENT DOCUMENTS

2004/0249272 A1* 12/2004 Carr ...................... A61B 18/18
600/430
2010/0286682 A1    11/2010 Podhajsky
(Continued)

FOREIGN PATENT DOCUMENTS

JP    2010-512214 A    4/2010
JP    2012-525920 A    10/2012

OTHER PUBLICATIONS

International Preliminary Report on Patentability issued from the International Preliminary Examining Authority in counterpart International Application No. PCT/EP2020/061764, mailed on Apr. 8, 2021.
(Continued)

*Primary Examiner* — Daniel W Fowler
(74) *Attorney, Agent, or Firm* — ArentFox Schiff LLP

(57) ABSTRACT

Various embodiments provide a microwave amplification apparatus for an electrosurgical instrument. The microwave amplification apparatus comprises: a cable assembly; a proximal launch portion, and a distal amplification portion. The proximal launch portion is connected to a proximal end of the cable assembly, and comprises: a DC source configured to launch a DC signal along the cable assembly, and a microwave source configured to launch a microwave signal along the cable assembly. The distal amplification portion is connected to a distal end of the cable assembly, and comprises: a power amplifier configured to receive the microwave signal as an input signal to be amplified. The distal amplification portion is configured to apply the DC signal as a drain voltage across the power amplifier. The power
(Continued)

FIG. 5 amplifier has an output that is connectable to deliver an amplified microwave signal to a structure that is configured to deliver microwave energy into biological tissue.

23 Claims, 4 Drawing Sheets

(51) Int. Cl.
*H03F 3/21* (2006.01)
*A61B 18/00* (2006.01)
(52) U.S. Cl.
CPC ............... *A61B 2018/00702* (2013.01); *A61B 2018/1861* (2013.01)
(58) Field of Classification Search
CPC .. A61B 2018/0063; A61B 2018/00785; A61B 2018/1823; A61B 2018/1861; A61B 2018/1869; A61B 2018/1876
See application file for complete search history.

(56) References Cited

U.S. PATENT DOCUMENTS

| | | | |
|---|---|---|---|
| 2011/0118724 A1* | 5/2011 | Turner | ............... A61B 18/1815 606/33 |
| 2011/0140607 A1* | 6/2011 | Moore | ..................... H05H 1/36 315/111.21 |
| 2012/0086682 A1 | 4/2012 | Shi | |

OTHER PUBLICATIONS

International Search Report and Written Opinion, issued by the International Searching Authority in corresponding International Application No. PCT/EP2020/061764, mailed on Jul. 10, 2020.
Search Report under Section 17(5), issued by the United Kingdom Intellectual Property Office in counterpart United Kingdom Application No. GB1906010.2, dated Oct. 18, 2019.

* cited by examiner

MICROWAVE AMPLIFICATION APPARATUS FOR AN ELECTROSURGICAL INSTRUMENT

CROSS-REFERENCE TO RELATED APPLICATIONS

This application is a National Stage entry of International Application No. PCT/EP2020/061764, filed on Apr. 28, 2020, which claims priority to United Kingdom Patent Application No. 1906010.2, filed on Apr. 30, 2019. The disclosures of the priority applications are hereby incorporated in their entirety by reference.

FIELD OF THE INVENTION

The invention relates to electrosurgical apparatus in which microwave frequency energy is used to treat biological tissue, e.g. to perform ablation or haemostasis (i.e. sealing broken blood vessels by promoting blood coagulation). It may be used in as part of a surgical apparatus which also delivers radiofrequency energy, e.g. for cutting tissue.

BACKGROUND TO THE INVENTION

Electromagnetic (EM) energy, and in particular microwave and radiofrequency (RF) energy, has been found to be useful in electrosurgical operations, for its ability to cut, coagulate, and ablate body tissue. Typically, apparatus for delivering EM energy to body tissue includes a generator comprising a source of EM energy, and an electrosurgical instrument connected to the generator, for delivering the energy to tissue. Conventional electrosurgical instruments are often designed to be inserted percutaneously into the patient's body. However, it can be difficult to locate the instrument percutaneously in the body, for example if the target site is in a moving lung or a thin walled section of the gastrointestinal (GI) tract. Other electrosurgical instruments can be delivered to a target site by a surgical scoping device (e.g. an endoscope) which can be run through channels in the body such as airways or the lumen of the oesophagus or colon. This allows for minimally invasive treatments, which can reduce the mortality rate of patients and reduce intraoperative and postoperative complication rates.

Tissue ablation using microwave EM energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating.

This principle is harnessed in microwave ablation therapies, where water molecules in target tissue are rapidly heated by application of a localised electromagnetic field at microwave frequencies, resulting in tissue coagulation and cell death. It is known to use microwave emitting probes to treat various conditions in the lungs and other organs. For example, in the lungs, microwave radiation can be used to treat asthma and ablate tumours or lesions.

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length. In the case of a bariatric patient the surgical accessory may have a length of 300 mm from handle to RF tip, whereas the equivalent distance in a laparoscopic case can be in excess of 2500 mm.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage then appears almost entirely across this void which ionises as a result, forming a plasma, which has a very high volume resistivity compared to tissue. This differentiation is important as it focusses the applied energy to the plasma that completed the electrical circuit between the cut pole of the RF blade and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

SUMMARY OF THE INVENTION

At its most general, the present invention provides a microwave amplification apparatus as part of an electrosurgical instrument located at the distal end of a flexible cable assembly, e.g. a cable assembly suitable for insertion through a patient's body to a treatment site, possibly through the instrument channel of a surgical scoping device, e.g. endoscope, bronchoscope, or the like. The cable assembly may provide a common pathway for a low power microwave signal and a DC signal. The microwave amplification apparatus includes a power amplifier that is arranged to amplify the low power microwave input to a power level that is suitable for treatment. In one example, the cable assembly may convey both a primary DC signal for providing a drain voltage of the power amplifier and a secondary DC signal for proving a bias voltage for the power amplifier. In another example, the microwave amplification apparatus includes circuitry at the distal end to derive a drain voltage and a gate voltage for the power amplifier from a single DC signal.

Both arrangements can be contrasted with conventional structures in which the microwave energy at a power level suitable for enabling treatment is generated at a proximal side and then conveyed by the cable assembly. The present arrangement can avoid the undesirable cable losses that can occur in the previous arrangement. This can be illustrated by example. If 10 W of power is wanted at the instrument and the cable exhibits 10 dB loss along its length, conventional system require an input power of 100 W. In such a system, 90 W of power is lost along the cable and the proximal amplifier must be capable of achieving an output power of 100 W or more. In contrast, by using an amplifier with a gain of 10 dB at the distal end, the apparatus of the invention can achieve an output of 10 W provided that the microwave signal received at the distal portion has a power of 1 W. With a cable loss of 10 dB, this requires the microwave signal to have a power of 10 W at the proximal end. The loss along the cable (9 W) in this scenario is thus an order of magnitude lower than conventional arrangements.

According to the invention, there is provided a microwave amplification apparatus for an electrosurgical instrument, the microwave amplification apparatus comprising: a cable assembly; a proximal launch portion connected to a proximal end of the cable assembly, the proximal launch portion comprising: a DC source configured to launch a DC signal along the cable assembly; and a microwave source configured to launch a microwave signal along the cable assembly; and a distal amplification portion connected to a distal end of the cable assembly, the distal amplification portion comprising: a power amplifier configured to receive the microwave signal as an input signal to be amplified, wherein the distal amplification portion is configured to apply the DC signal as a drain voltage across the power amplifier, and wherein the power amplifier has an output that is connectable to deliver an amplified microwave signal to a structure that is configured to deliver microwave energy into biological tissue. In this apparatus, the DC signal is manipulated to enable operation of a power amplifier at the distal end of the cable assembly. The apparatus therefore operates without conveying high power microwave signals along a cable assembly.

The apparatus may include a gate voltage extraction module configured to extract a bias voltage from the DC signal and apply it to a gate of the power amplifier. The gate voltage extraction module may be in the distal amplification portion or the proximal launch portion. When in the proximal launch portion, the DC signal may comprises two separate components: a primary DC signal corresponding to a drain voltage of the power amplifier, and a secondary DC signal corresponding to the bias voltage of the power amplifier. The separate components may be conveyed by independent transmission lines in the cable assembly.

The cable assembly may comprise a coaxial transmission line that comprises an inner conductor separated from an outer conductor by a dielectric material. The microwave signal may be conveyed by the coaxial transmission line. Advantageously, the DC signal may be conveyed along the inner conductor, whereby a common transmission line structure is used to convey both the microwave signal and the DC signal. In other examples, the DC signal may be conveyed by a separate transmission line in the cable assembly. Where the DC signal has two components, one component (e.g. the secondary DC signal) may be transmitted on the inner conductor of the coaxial transmission line, while the other is transmitted on a separate transmission line.

The microwave signal may be coupled into the coaxial transmission line via a capacitor. This avoids the DC signal from leaking back into the microwave source. The DC source may include a low pass filter to prevent the microwave signal from leaking into it.

The output of the power amplifier may include a capacitor configured to couple the amplified microwave signal to the structure. The capacitor acts as a DC isolator to prevent the DC signal from travelling into the structure for delivered the microwave energy into biological tissue. The capacitor may thus protect a patient from the DC signal.

The gate voltage extraction module may comprise a DC-DC converter configured to down convert a voltage of the DC signal to generate the bias voltage. For example, the DC-DC converter may comprise a buck converter.

In one embodiment, the gate voltage extraction module may be configured to extract a pair of bias voltages from the DC signal. The pair of bias voltages may comprise a first bias voltage corresponding to a non-conducting state of the power amplifier, and a second bias voltage corresponding to a conducting state of the power amplifier. For example, the gate voltage extraction module may comprise a pair of buck converters connected in parallel, wherein the pair of buck converters comprises a first buck converter for generating the first bias voltage, and a second buck converter for generating the second bias voltage. The apparatus may further comprise a gate control module configured to selectively apply the first bias voltage or the second bias voltage to the gate of the power amplifier. For example, the gate control module may be configured to apply the first bias voltage (to ensure the power amplifier is non-conducting and therefore not providing any gain to an input signal) as a default condition, which can be overridden to apply the second bias voltage in certain circumstances (i.e. when tissue treatment is wanted). For example, the gate control module may comprise a switch arranged to selectively apply the first bias voltage or the second bias voltage to the gate of the power amplifier. The distal amplification portion may comprises a voltage rail arranged to adopt an operational voltage provided by the DC signal. The switch may be configured to select the second bias voltage upon application of the operational voltage to the voltage rail. In other words the switch is operatively connected to the voltage rail, wherein actuation of the switch is dependent on the voltage on the voltage rail. When the voltage on the voltage rail is below a threshold (e.g. indicating absence of the DC signal), the switch adopts the default position and the power amplifier resides in a non-conducting state.

The gate control module may further comprise a delay circuit arranged to introduce a time lag between application of the operational voltage to the voltage rail and actuation of the switch to select the second bias voltage.

The gate extraction voltage module may be configured to cause the first bias voltage and the second bias voltage both to have a polarity that is opposite to the drain voltage. In one example, the drain voltage is 28 V, the first bias voltage is −6 V, and the second bias voltage is −2 V. In this example, the second bias voltage is selected to be close to the transition to a conducting state in the characteristic of the power amplifier.

The microwave signal may have a power equal to or less than 1 W at the proximal end of the cable assembly. However, the amplified microwave signal may have a power equal to or greater than 5 W, e.g. equal to or greater than 10 W.

The distal amplification module may include isolation structure to protect the component handling the DC signal from the microwave signal. For example, distal amplification module may include a low pass filter connected between the gate voltage extraction module and the gate of the power amplifier. The low pass filter may be fabricated on a microstrip transmission line. The low pass filter may comprise a pair of quarter wave stubs that each have a length of $$\frac{(2n-1)\lambda}{4},$$

wherein the pair of quarter wave stubs comprises a first quarter wave stub located at a distance $$\frac{n\lambda}{2}$$

from the gate of the power amplifier, and a second quarter wave stub spaced from the first quarter wave stub by a distance $$\frac{n\lambda}{2},$$

where $\lambda$ is the wavelength of the microwave signal, and n is a whole number equal to 1 or more.

The distal amplification portion comprises a voltage rail arranged to adopt an operational voltage provided by the DC signal, wherein the voltage rail is connected to a distal end of the cable assembly by a first connection line to receive the DC signal, wherein the voltage rail is connect to a drain of the power amplifier by a second connection line to provide the drain voltage. The voltage rail may be protected from the microwave signal in a similar manner to the gate voltage extraction module, by suitable positioning of low pass filters. For example, there may be a proximal low pass filter on the first connection line and a distal low pass filter on the second connection line. The proximal low pass filter comprises a pair of quarter wave stubs that each have a length of $$\frac{(2n-1)\lambda}{4},$$

wherein the pair of quarter wave stubs comprises a first quarter wave stub located at a distance $$\frac{n\lambda}{2}$$

from a connection point between the first connection line and the cable assembly, and a second quarter wave stub spaced from the first quarter wave stub by a distance $$\frac{n\lambda}{2},$$

where $\lambda$ is the wavelength of the microwave signal, and n is a whole number equal to 1 or more. The distal low pass filter comprises a pair of quarter wave stubs that each have a length of $$\frac{(2n-1)\lambda}{4},$$

wherein the pair of quarter wave stubs comprises a first quarter wave stub located at a distance $$\frac{n\lambda}{2}$$

from the drain of the power amplifier, and a second quarter wave stub spaced from the first quarter wave stub by a distance $$\frac{n\lambda}{2},$$

where $\lambda$ is the wavelength of the microwave signal, and n is a whole number equal to 1 or more.

In another aspect, there is provided an electrosurgical instrument comprising: a microwave amplification apparatus as set out above; and a radiating tip connected to the output of the power amplifier, wherein the radiating tip comprises an antenna configured to radiate the amplified microwave signal into biological tissue. Any suitable antenna structure may be used. For example, the radiating tip may have a coaxial structure, in which an inner conductor extends beyond a distal end of an outer conductor to form the antenna. Alternatively, the radiating tip may have a planar structure, comprising a planar piece of insulating dielectric having layers of metallization on opposing surfaces. The layers of metallization may be configured to operate as an antenna.

The microwave amplification apparatus and radiating tip may be dimensioned to be insertable through an instrument channel of a surgical scoping device.

The radiating tip may be configured to receive additional inputs, e.g. radiofrequency energy. The radiating tip may include a means (e.g. a needle or the like) for delivering fluid to a treatment site.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate instrument. In use, the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Preferred spot frequencies for microwave EM energy include: 915 MHz, 2.45 GHz, 3.3 GHz, 5.8 GHz, 10 GHz, 14.5 GHz and 24 GHz. 5.8 GHz may be preferred. The device may deliver energy at more than one of these microwave frequencies.

The term "radiofrequency" or "RF" may be used to indicate a frequency between 300 kHz and 400 MHz.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Background—Electrosurgical Apparatus

Figure 1:
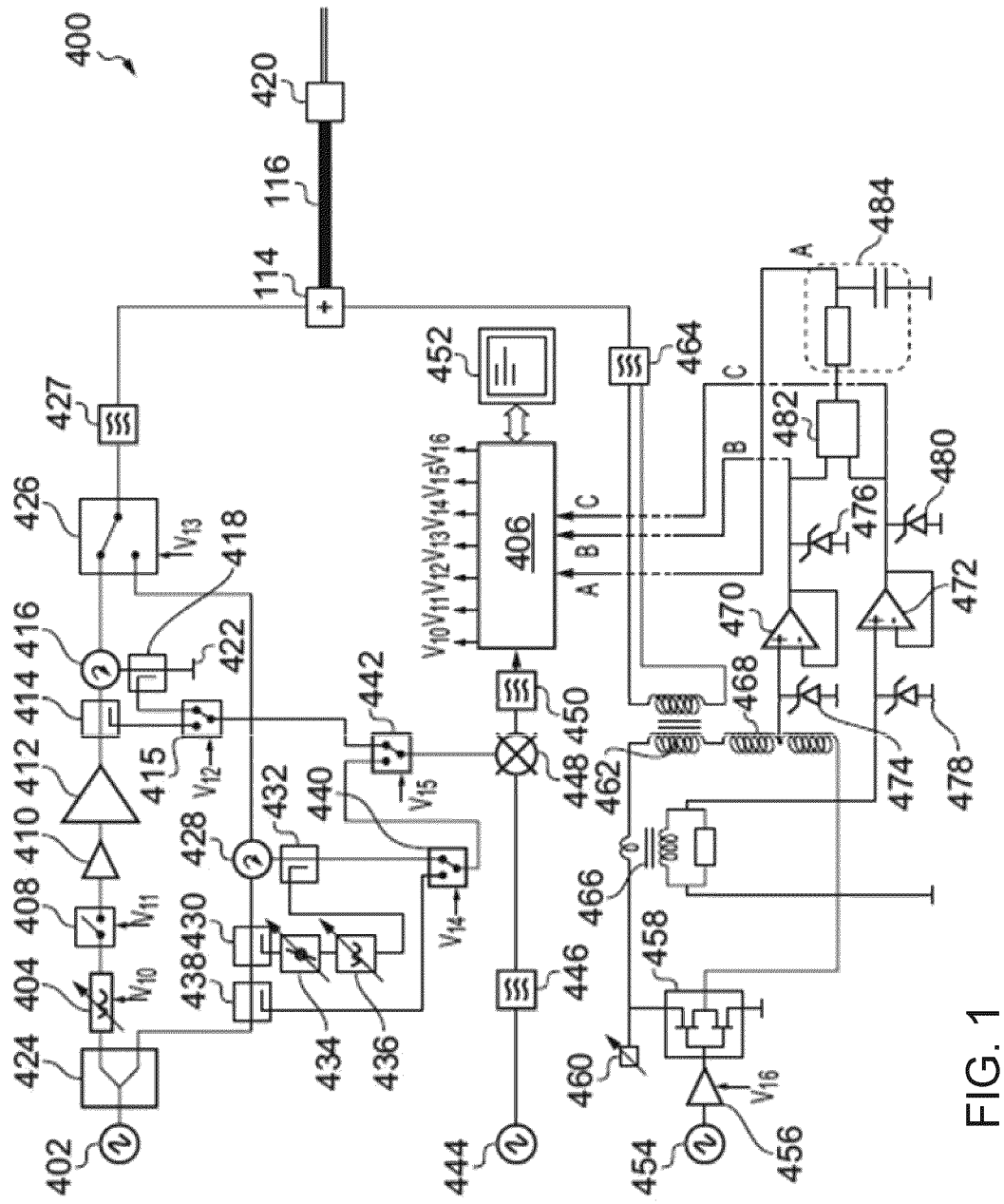
FIG. 1 is an overall schematic system diagram of an electrosurgical apparatus is aid understanding of the present invention.

FIG. 1 shows a schematic diagram of an electrosurgical apparatus 400 such as that disclosed in GB 2 486 343 that is useful for understanding the invention. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue. As explained in more detail below, the present invention provides a means of supplying microwave energy that can replace the microwave channel in this apparatus.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection.

The other branch from the power splitter 424 forms a measurement channel. The measurement channel bypasses the amplifying line-up on the microwave channel, and hence is arranged to deliver a low power signal from the probe. A primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit may be used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connected to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452.

The RF channel shown in FIG. 1 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 1).

To derive phase information, the voltage and current signals (B and C) are also connected to a phase comparator 482 (e.g. an EXOR gate) whose output voltage is integrated by RC circuit 484 to produce a voltage output (shown as A in FIG. 1) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420, from which it is delivered (e.g. radiated) into the biological tissue of a patient. The cable assembly 116 may be insertable through the entire length of an instrument (working) channel of a surgical scoping device (not shown). The probe 420 may be shaped to pass through the instrument channel of the surgical scoping device and protrude (e.g. inside the patient) at the distal end of the endoscope's tube. The probe 420 may include an active tip for delivering RF EM energy and/or microwave EM energy into biological tissue and a retractable hypodermic needle for delivering fluid. These combined technologies provide a unique solution for cutting and destroying unwanted tissue and the ability to seal blood vessels around the targeted area.

A waveguide isolator (not shown) may be provided at the junction between the microwave channel and signal combiner 114. The waveguide isolator may be configured to perform three functions: (i) permit the passage of very high microwave power (e.g. greater than 10 W); (ii) block the passage of RF power; and (iii) provide a high withstanding voltage (e.g. greater than 10 kV). A capacitive structure (also known as a DC break) may also be provided at (e.g. within) or adjacent the waveguide isolator. The purpose of the capacitive structure is to reduce capacitive coupling across the isolation barrier.

Background—Electrosurgical Instrument

Figure 2:
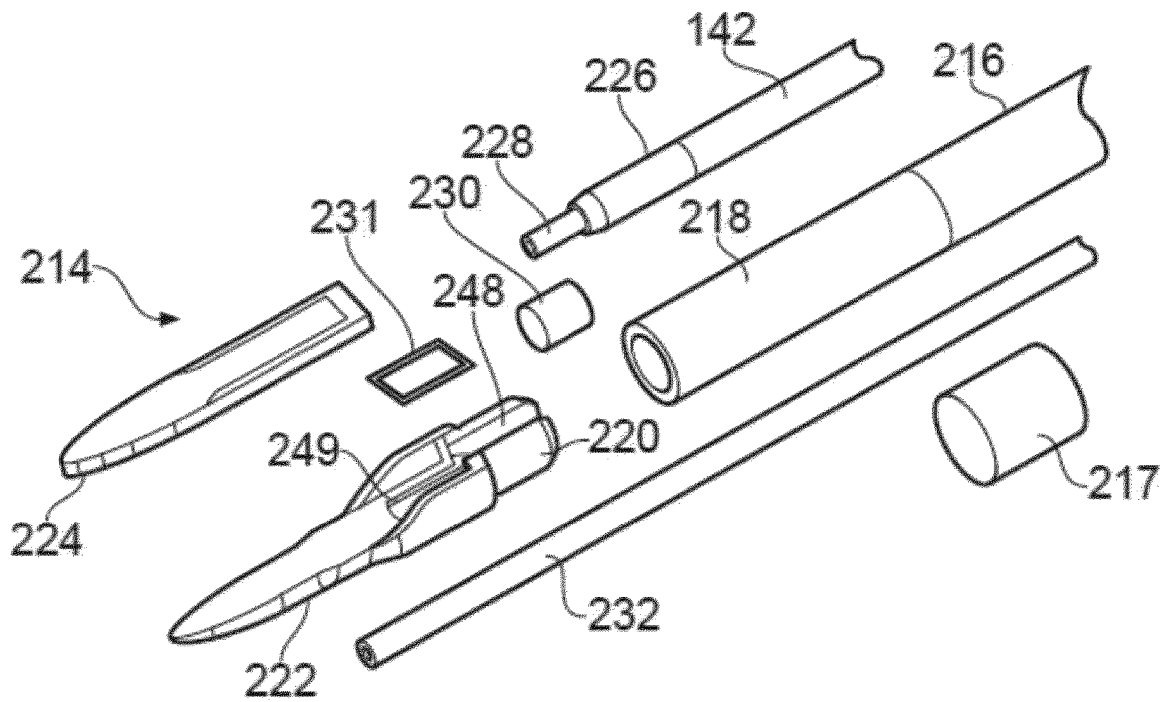
FIG. 2 is an exploded view of a distal end of an electrosurgical instrument in which the present invention may be used.

FIG. 2 shows an exploded view of an example probe 214 (sometimes referred to as a distal end assembly or an instrument tip), which is an electrosurgical instrument to which the present invention may be applied. The probe 214 is mounted at the distal end of an outer cannula tube 216 of a flexible shaft, e.g. which corresponds to the cable assembly 116 discussed above with reference to FIG. 1. The cannula tube 216 forms a flexible sleeve defining a lumen for transporting fluid to the instrument tip, the instrument tip being secured at its distal end. In order to provide a torque transfer function, the outer cannula tube 216 is formed of a braided tube, e.g. comprising a braided wire (e.g. stainless steel) wrap mounted between a radially inner polymer layer and a radially outer polymer layer, wherein the polymer may be e.g. Pebax®.

The outer cannula tube 216 is connected at its distal end to an unbraided tubular portion 218, which may be a flexible conduit. The tubular portion 218 may be formed from any suitable polymer material, e.g. Pebax® or the like. The tubular portion 218 may have an axial length (i.e. length in line with the shaft axis equal to or greater than 1 mm. This may ensure that a safe distance is introduced between the end of the braiding and the proximal edge of the distal end assembly 214 in order to avoid any risk of heating of the braid as a result of capacitive conductance during use of microwave energy. This arrangement may also prevent the two plates of the planar transmission line or the two conductors in the coaxial transmission line from becoming shorted or connected together.

The tubular portion 218 may be referred to as a 'soft tip' 218. The soft tip 218 may in some examples be an additional length of polymer tube which is bonded to the distal end of the sleeve or cannula tube 216. The bonding may use any suitable adhesive, e.g. epoxy or the like. A support tube 217 may be mounted over the junction between the tubular portion 218 and cannula tube 216 to reinforce the joint by providing additional mechanical strength. The support tube 217 may be a short section of polymer tubing within which the both the tubular portion 218 and the cannula tube 216 are secured, e.g. by bonding. The support tube 217 may be flexible and/or may have a length selected to ensure that it does not adversely affect the flexibility of the shaft.

The junction of the tubular portion 218, cannula tube 216 and support tube 217 may also be captured within a heat shrink sleeve (not shown) to provide further structural strength at the distal end of the shaft.

The braiding within the cannula tube 216 enables torque applied to the proximal end of the shaft to be transformed into rotational movement of the instrument tip.

A distal end of the tubular portion 218 is arranged to fit over a corresponding proximal part 220 of a protective hull 222. The protective hull 222 is formed from a rigid material having low friction with biological tissue, e.g. stainless steel. The hull 222 is preferably formed from a metallic material, but may be formed from non-metallic materials, e.g. ceramic. The hull is shaped to perform a number of functions:

to secure the distal end assembly 214 to the cannula tube 216, to provide a protective undersurface for an active tip structure that delivers energy into surrounding biological tissue, to provide a protective housing and supporting frame for a retractable needle, and to locate the active tip structure relative to the coaxial cable during assembly and subsequent use.

The parts of the structure of the hull 222 that perform these functions are discussed in more detail below.

Figure 3:
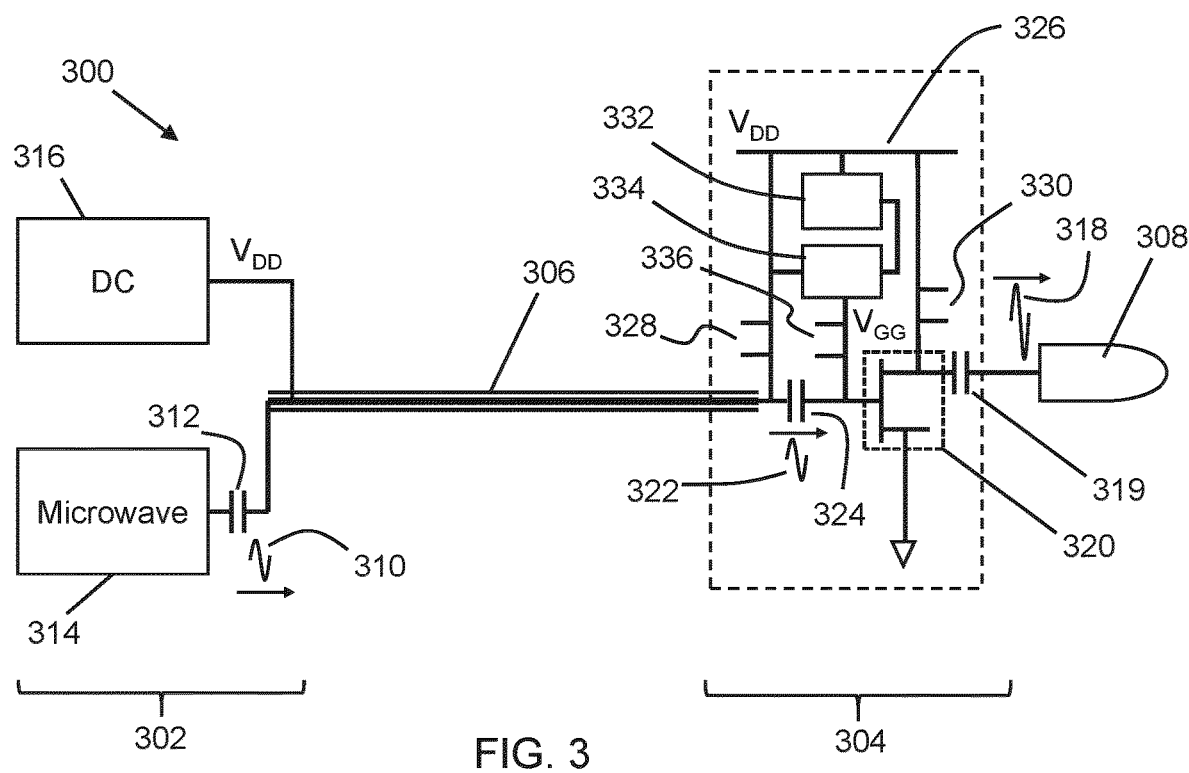
FIG. 3 is a schematic diagram of a distal instrument-based microwave generation module that is an embodiment of the invention.
Figure 4:
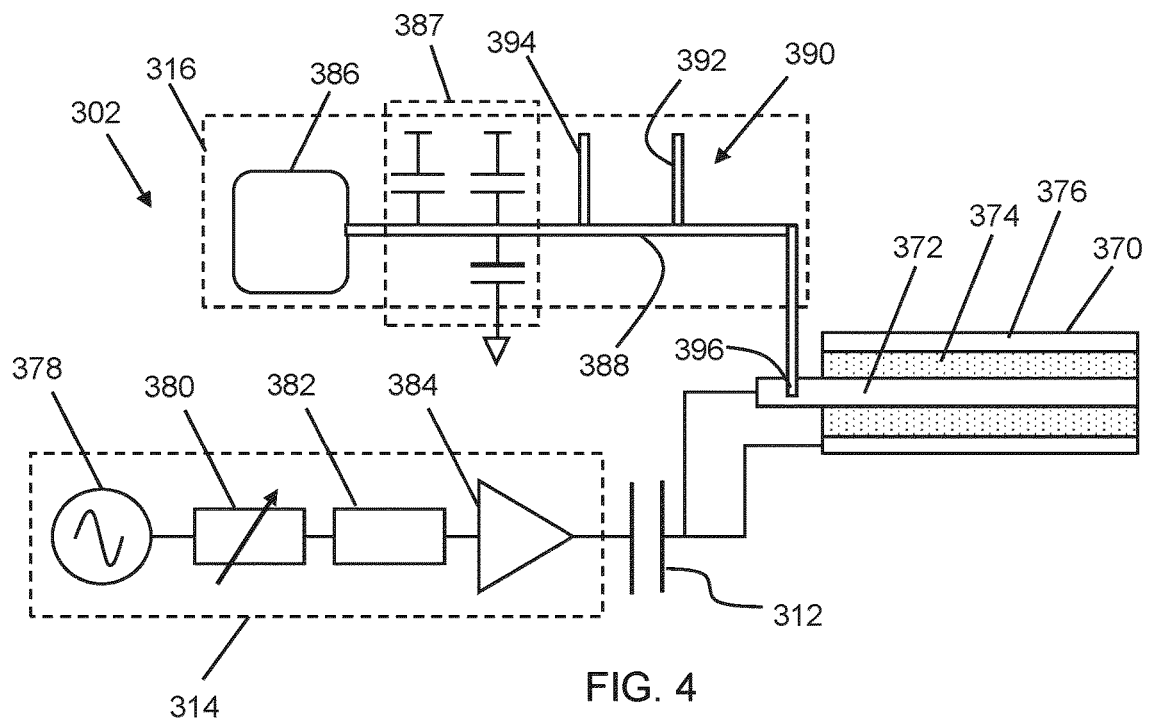
FIG. 4 is a schematic diagram of components for launching DC power and low power microwave energy into a proximal end of a coaxial transmission line.
Figure 5:
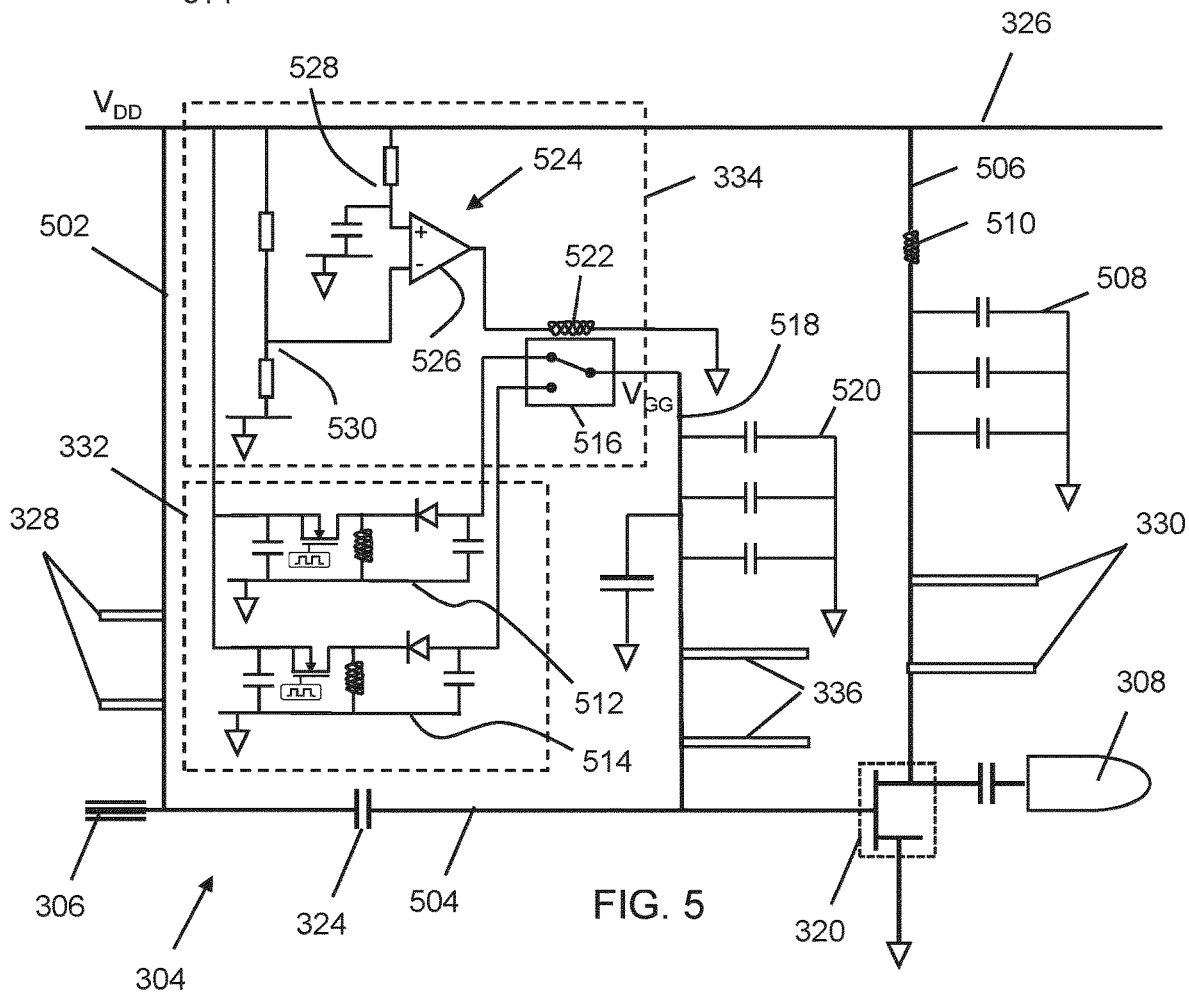
FIG. 5 is a schematic circuit diagram showing a distal microwave amplification module for an embodiment of the invention.

In an embodiment of the invention, the protective hull 222 is further configured to house distal components of the microwave generation circuitry (also referred to herein as a distal microwave generation module), as discussed in more detail with respect to FIGS. 3 to 5.

The distal end assembly 214 includes an active tip 224, which is a planar piece of dielectric material 221 (e.g. alumina) having conductive layers (e.g. layers of metallisation) on its upper and lower surfaces. The conductive layers are each electrically connected to a respective one of an inner conductor 228 and an outer conductor 226 of a coaxial cable 142 that is conveyed by the cannula tube 216. At a distal end of the coaxial cable 142, its outer sheath is removed to expose a length of the outer conductor 226. The inner conductor 228 of the coaxial cable extends beyond the distal end of the outer conductor 226. The coaxial cable 142 and the active tip 224 are mounted relative to one another so that the protruding part of the inner conductor 228 lies on a first conductive layer of the active tip, while the outer conductor 226 is brought into electrical connection with a second conductive layer via the protective hull 222, as discussed below. The first conductive layer is isolated from the outer conductor 226 and the second conductive layer is isolated from the inner conductor 228.

The conductive layers may be formed from high melting point conductors, e.g. W or Ti. However, in one example, to facilitate the use of solder in the electrical connection between the inner and outer conductors of the coaxial cable 142 and the active tip 224, lower melting point conductors may be deposited at proximal regions on the conductive layers where the electrical connections are made. The lower melting point conductors may be silver (Ag) or gold (Au).

The distal end of the active tip 224 is curved to avoid presenting sharp corners within the patient.

The outer conductor 226 is electrically connected to a lower conductive layer on the underside of the active tip 224 via the protective hull 222. A proximal end of the protective hull 222 is formed with a U-shaped channel 248 for receiving and supporting a distal end of the coaxial feed cable 142. The distal end assembly is configured so that the exposed portion of the outer conductor 226 sits in the U-shaped channel 248. An electrically conductive element 230, such as a sleeve or collar, is used to crimp the exposed portion of the outer conductor 226. The compression caused by the crimp means that the coaxial cable deforms in the region where it is received by the protective hull 222. For example, the portion of the coaxial cable where the outer conductor 226 is exposed may have an oval cross-section, whereby it abuts and forms a robust electrical contact with the sides of the U-shaped channel 248. The crimped outer conductor 226 may thus be retained by the hull via an interference fit.

To complete the electrical connection between the outer conductor 226 and lower conductive layer 229 on the active tip 224, the protective hull 222 is electrically coupled to the lower conductive layer, e.g. by soldering (see e.g. FIG. 5). In this embodiment, a solder preform 231 is provided for this purpose. the solder preform 231 is shaped to be receivable within a recess 249 formed in an upper surface of the protective hull 222. In this example, the recess 49 is rectangular, and the solder preform 231 has a corresponding shape, but any suitable shape may be used. The recess 249 is set back from the edges of the protective hull in a manner that ensures solder is only present between the lower surface of the active tip 224 and the protective hull 222, i.e. it does not flow to the side edges of the active tip 224. When assembled, the solder preform 231 may be aligned with a region on the lower surface of the active tip 224 that is coated in a lower melting point conductor as discussed above (e.g. gold). A suitable flex (not shown) may be provided with the solder preform when the components are assembled to facilitate the soldering process. The soldering process itself may be induction soldering. The induction soldering effect may be confined to a region of the active tip 224 and protective hull 222 at the solder preform 231.

The above configuration is advantageous because the protective hull 222 retains all of (i) the active tip 224, (ii) the solder preform 231, and (iii) the coaxial cable 142 in a fixed spatial relationship which ensures accurate and repeatable assembly.

In an embodiment of the invention, the connection between a distal portion of the coaxial cable 142 and the active tip 224 may be made via a distal microwave generation module, as discussed in more detail below.

The distal end assembly further comprises a needle guide 232 that is retained within a recess formed in the undersurface of the protective hull 222. The needle guide 232 is a hollow tube (e.g. a ferrule), e.g. made of polyimide, within which a hypodermic needle 234 is slidably mounted. The needle 234 is in fluid communication with the internal volume of the cannula tube 216 in order to receive liquid present therein for delivery to the treatment site.

After the distal end assembly 214 is assembled, it may be secured within the distal end of the tubular portion 218 by an interference fit and an adhesive (e.g. epoxy). The adhesive may also form a plug for the distal end of the tubular portion 218 to provide a fluid tight seal that means the only exit for fluid introduced at the interface joint is through the needle 234. Similarly, the junction (e.g. soldered joint) between the inner conductor 228 and the upper conductive layer 227 may have a protective cover 251 (see FIG. 5) that may be formed from a suitable adhesive (e.g. epoxy). The protective cover 251 may strengthen the connection between the protective hull 222 and active tip 224, while also forming an end plug for the tubular portion 218, i.e. a fluid tight seal that means the only exit for fluid introduced at the interface joint is through the needle.

In use the active tip 224 makes an intimate contact with the patient. The needle 234 can be extended beyond the distal end of the active tip 224 and retracted to a position back inside the guide tube 232 via control of the slider mechanism on the interface joint which acts on a control wire 235 to deploy and retract the needle 234. In its extended position, the needle is used to inject fluid for the purpose of locally distending and/or marking tissue. The conductive layers on the active tip 224 form bi-polar electrodes for delivering RF and/or microwave electromagnetic energy.

The needle guide 232 extends back inside and proximal to the distal assembly to provide extended creepage clearance to ensure RF/microwave activation only occurs across the distal tip region of the active tip 224.

Instrument-Based Microwave Amplification

FIG. 3 shows a microwave generation apparatus 300 that is an embodiment of the invention. The microwave generation apparatus 300 has a proximal launch portion 302 and a distal amplification portion 304 separated by a flexible cable assembly 306. The cable assembly 306 may correspond to the cable assembly 116 discussed above with respect to FIG. 1.

The proximal launch portion 302 functions to launch both DC power and a microwave signal 310 into the cable assembly 306. The cable assembly 306 comprises a coaxial transmission line for conveying the microwave signal 310 to the distal amplification portion 304. The cable assembly 306 may include an independent elongate conductor (e.g. wire) for conveying the DC power to the distal amplification portion 304. However, advantageously, the DC power may be launched on an inner conductor of the coaxial transmission line that carries the microwave signal 310.

The proximal launch portion 302 comprises a DC power generator 316 for generating the DC power. The DC power generator 316 may output a DC signal having a voltage $V_{DD}$ of 28 V, for example.

The proximal launch portion 302 comprises a microwave signal generator 314 arranged to produce the microwave signal 310. The microwave signal generator 314 is described below with reference to FIG. 4. The microwave signal 310 from the microwave signal generator 314 is coupled to the coaxial transmission line via a capacitor 312, which acts as a DC isolation barrier to prevent the DC signal from the DC power generator 316 from leaking into the microwave signal generator 314.

The microwave signal 310 from the microwave generator 314 may have a power level that is less than that require to treat (e.g. ablate or coagulate) biological tissue. For example, the microwave signal 310 output from the microwave generator 314 may have a power level equal to or less than 10 W. If the cable assembly exhibits a 10 dB loss along its length, this means that the power of the microwave signal 322 at the distal end is 1 W. If the power amplifier 320 exhibits a gain of 10 dB, the power available for treatment is thus 10 W.

Transmitting a low power microwave signal from the microwave signal generator means that less power is lost during transmission through the cable assembly 306. This avoids or reduces heating of the cable assembly 306 due to microwave losses, and therefore avoids the risk of accidental tissue heating along the path of the cable assembly.

The distal amplification portion 304 functions to amplify the microwave signal 310 received from the cable assembly 306 to a power level suitable for treatment. The amplified microwave signal 318 is output by the distal amplification portion 304, whereupon it is coupled via capacitor 319 to an instrument tip 308, such as the active tip 224 discussed above, from which it is delivered (e.g. radiated or otherwise emitted) into biological tissue at a treatment site. The capacitor 319 operates as a DC barrier between the instrument tip 308 and distal amplification portion 304 to prevent the DC signal from reaching the instrument tip.

The distal amplification portion 304 includes a power amplifier 320, e.g. a power MOSFET or the like. The power amplifier 320 receives as an input the microwave signal 322 output from the coaxial transmission line. The input to the power amplifier 320 is protected from the DC signal in the cable assembly 306 by a capacitor 324.

The distal amplification portion 304 is arranged to separate the DC power from the microwave signal, and apply it across the power amplifier 320. The distal amplification portion 304 may include a voltage rail 326 to which the DC signal ($V_{DD}$) is applied. The microwave signal 322 may be blocked from the voltage rail 326 by filtering arrangement 328, which may comprises a pair of quarter wave stubs as discussed in more detail below. Similarly a filtering arrangement 330 may also be disposed on the connection between the voltage rail 326 and power amplifier 320 to prevent microwave energy from leaking out on the voltage rail 326 from the power amplifier 320.

The distal amplification portion 304 further comprises a gate voltage extraction module 332 that operates to derive from the DC signal a bias voltage $V_{GG}$ to be applied to the gate of the power amplifier 320. The gate voltage extraction module 332 may include a DC-DC converter, which down-converts the DC signal voltage to a suitable level for the power amplifier 320.

The distal amplification portion 304 may further comprise a gate control module 334 for controlling application of the gate voltage to the power amplifier 320. As discussed in more detail below, the gate control module 334 may operate to switch between two bias voltage states, which correspond respectively to an ON (conducting) and OFF (non-conducting) condition for the power amplifier 320. The gate control module 334 may operate to introduce a time delay between application of the DC signal across the power amplifier 320 (i.e. as its drain voltage) and application of a bias voltage to turn on the power amplifier 320 in order to ensure a smooth initialisation of the amplification process.

A filtering arrangement 336 may be disposed on the connection between the gate control module 334 and the gate of the power amplifier 320 to prevent microwave energy from leaking into the gate control module 334 from the power amplifier 320.

Detailed structures for the gate voltage extraction module 332 and gate control module 334 are discussed below with reference to FIG. 5.

In use, the microwave generation apparatus 300 thus performs the amplification of a low power input microwave signal to a power level suitable for treatment. The amplified power level may be one or more orders of magnitude higher than the input power level, e.g. 10 W or more. With this arrangement, there is much low loss of power along the cable assembly 306, which in turn means a reduction in the risk of accidental heating of tissue along the path taken by the cable assembly 306.

The distal amplification portion 304 may be located in the distal end assembly 214 as shown in FIG. 2. For example, the distal amplification portion 304 may be disposed between a proximal end of the active tip 224 and a distal end of the coaxial cable 142. The protective hull 222 may be or may have mounted thereon a substrate (e.g. PCB or the like) to support the components of the distal amplification portion 304.

FIG. 4 is a schematic diagram of an example of a proximal launch portion 302, in which a microwave signal and a DC signal are launched into a proximal end of a coaxial transmission line 370. Features in common with FIG. 3 are given the same reference number and are not described again. The coaxial transmission line 370 comprises an inner conductor 372 separated from an outer conductor 376 by a dielectric material 374. The coaxial transmission line 370 may be a Sucoform cable manufactured by Huber+Suhner, for example.

FIG. 4 shows components for the microwave signal generator 314. In this example, microwave signal generator 314 has a microwave frequency source 378 followed by a variable attenuator 380, which may be controlled by a controller (not shown) via a control signal in a similar way to the system shown in FIG. 1. The output of the variable attenuator 380 is input to a signal modulator 382, which may also be controlled by the controller, e.g. to apply a pulsed waveform to the microwave signal. The output from the signal modulator is input to a drive amplifier 384 to generate the microwave signal at the desired power level for transmission to the distal amplification portion. The microwave signal is coupled to the coaxial transmission line 370 via a capacitor 312.

The DC power generator 316 comprises a voltage source 386 that is connected to apply a DC voltage to the inner conductor 372 of the coaxial transmission line 370. The voltage source 386 may be a switched mode power supply, or to enable the apparatus to be portable, a battery may be used. The connection may be or may include a section of microstrip transmission line 388 on which a low pass filter 390 is provided to prevent back transmission of the microwave signal into the voltage source 386. The low pass filter 390 comprises a pair of quarter wave stubs 392, 394 on the microstrip transmission line 388. A first stub 392 is located at a half wavelength $$\left(\text{i.e. } \frac{n\lambda}{2}\right)$$

distance from a connection point 396 to the inner conductor 372 of the coaxial transmission line 370, where λ is the wavelength of the microwave signal on the microwave transmission line 388, and n is a whole number equal to 1 or more. This ensure that the base of the first quarter wave $$\left(\text{i.e. } \frac{(2n-1)\lambda}{4}\right)$$

stub 392 is at a short circuit condition, so that the other end of the quarter wave stub 392 is in an open circuit condition. A second quarter wave stub 394 is spaced from the first stub by a half wavelength $$\left(\text{i.e. } \frac{n\lambda}{2}\right)$$

distance.

The DC power generator 316 further comprises a set of capacitors 387 connected in shunt to the transmission line that conveys the DC signal in order to remove any other unwanted AC element on the DC signal path.

FIG. 5 is a schematic circuit diagram showing a distal microwave amplification module 304 for an embodiment of the invention. Features in common with the previous drawings are given the same reference number and are not described again.

In this example, a distal end of the cable assembly 306 is connected to the distal microwave amplification module 304. The cable assembly 306 may include the coaxial transmission line 370 discussed above, which conveys both the microwave signal and the DC signal. The distal microwave amplification module 304 splits the microwave signal from the DC signal using filters. The DC signal passes to the DC rail 326 via a first connection line 502, which has a low pass filter comprising a pair of quarter wave stubs 328 arranged to prevent passage of the microwave signal.

The pair of stubs 328 may be fabricated on a microstrip transmission line. A first stub is located at a half wavelength $$\left(\text{i.e. } \frac{n\lambda}{2}\right)$$

distance from a connection point to the inner conductor of the coaxial transmission line, where λ is the wavelength of the microwave signal on the microwave transmission line, and n is a whole number equal to 1 or more. This ensure that the base of the first quarter wave $$\left(\text{i.e. } \frac{(2n-1)\lambda}{4}\right)$$

stub is at a short circuit condition, so that the other end of the quarter wave stub is in an open circuit condition. A second quarter wave stub is spaced from the first stub by a half wavelength $$\left(\text{i.e. } \frac{n\lambda}{2}\right)$$

distance.

Meanwhile the microwave signal passes to a power amplifier 320 along connection line 504, where it becomes an input signal to be amplified. The connection line 504 may be a microstrip transmission line or the like. The connection line 504 includes a capacitor 324 through which the microwave signal is coupled but which blocks the DC signal. The capacitor 324 therefore isolates the power amplifier 320 from any DC component conveyed from the coaxial transmission line 370 in the cable assembly 306.

A connection line 506 connects the voltage rail 326 to the power amplifier 320 to apply a voltage of the DC signal across the power amplifier 320 (i.e. as a drain supply). To prevent microwave energy from leaking out of the power amplifier 320 on the connection line 506, a pair of quarter wave stubs 330 are arranged as a low pass filter. The pair of stubs 330 may be arranged in a similar manner to the stubs 328, albeit with respect to a connection point between the connection line 506 and the power amplifier 320.

The connection line 506 further comprises a set of capacitors 508 connected in shunt to the connection line that conveys the DC signal in order to remove any other unwanted AC element on the DC signal path.

The connection line 506 further comprises an inductor 510 connected in series between the power amplifier 320 and voltage rail 326. The inductance further inhibits leakage of AC signals onto the voltage rail 326.

Each of the connection lines discussed above may be implemented as a suitable transmission line for conveying DC or microwave signals as appropriate. Microstrip lines, e.g. on a flexible substrate that can be wrapped into a compact configuration are a suitable example.

In this embodiment, the distal microwave amplification module 304 is configured to extract a bias voltage $V_{GG}$ for the power amplifier from the voltage rail 326. The voltage rail 326 may be at a relatively high voltage, e.g. 28 V or similar, whereas the bias voltage for the power amplifier 320 may need to be an order of magnitude lower. To obtain the bias voltage, the distal microwave amplification module 304 includes a gate voltage extraction module 332. The gate voltage extraction module 332 functions as a DC-DC converter, and in this embodiment it is implemented as a pair of parallel buck converters 512, 514, each of which is configured to output a different voltage, so that the bias voltage can be switched between two different states.

Each buck converter 512, 514 is connected to the voltage rail 326 to provide an input voltage. The values of the capacitance and inductance within each buck converter 512, 514 are selected to transform the input voltage to a desired output voltage. The output voltages may be selected based on the operational characteristic of the power amplifier. In this example, the buck converters 512, 514 are configured to generate a negative output voltage by using a diode to control an appropriate current flow direction in each converter. This means the output voltages (bias voltages) can be set close to the point in its characteristic where the power amplifier enters a conducting state.

For example, a first buck converter 512 may be configured to output a bias voltage that lies in a non-conducting part of the power amplifier characteristic, e.g. −6 V. A second buck converter 514 may be configured to output a bias voltage that lies in a conducting part of the power amplifier characteristic, preferably just beyond a transition to the conducting state, e.g. −2 V.

The outputs from the pair of buck converters 512, 514 are connected to respective input poles of a switch 516 that forms part of a gate control module 334. An output of the switch 516 is connected to a connection line 518 which in turn is connected to connection line 504 to provide the bias voltage from the gate voltage extraction module 332 to a gate of the power amplifier 320.

To prevent microwave energy from leaking out of the power amplifier 320 on the connection line 518, a pair of quarter wave stubs 336 are arranged as a low pass filter. The pair of stubs 336 may be arranged in a similar manner to the stubs 328, albeit with respect to a connection point between the connection line 518 and the connection line 504.

The connection line 518 further comprises a set of capacitors 520 connected in shunt to the connection line 518 that conveys the bias voltage in order to remove any other unwanted AC element on the bias voltage signal path.

The gate control module 334 operates to apply a required bias voltage to the gate of the power amplifier 320. The gate control module 334 thus effectively operates to selectively activate the power amplifier 320. In this example, the gate control module 334 functions to control the switch 516 that selects the buck converter 512, 514 to provide the bias voltage to the power amplifier 320. The switch 516 may be controlled by an inductor 522 that is energised upon application of the DC signal to the voltage rail 326. The switch 516 may thus adopt a default (e.g. OFF) configuration when the inductor 522 is not energised. In this configuration, the switch 516 connects the buck converter with the non-conducting voltage level (e.g. −6 V) to the power amplifier. When the inductor 522 is energised, the switch adopts an activated (e.g. ON) configuration, in which the buck converter with the conducting voltage level (e.g. −2 V) is connected to the power amplifier.

In this embodiment, the gate control module 334 includes a 'soft-start' circuit 524 for the power amplifier 320, which acts to delay the change of state of the switch by smoothly increasing the voltage applied to the inductor 522. An advantage of this arrangement is that it enables the drain voltage across the power amplifier 320 to reach a steady state before a bias voltage to activate the power amplifier is applied. The 'soft-start' circuit 524 is implemented using a comparator 526 which generates an output to the inductor 522 based on a difference between a varying first input from an RC circuit 528 and a fixed input from a voltage divider circuit 530.

Figure 6:
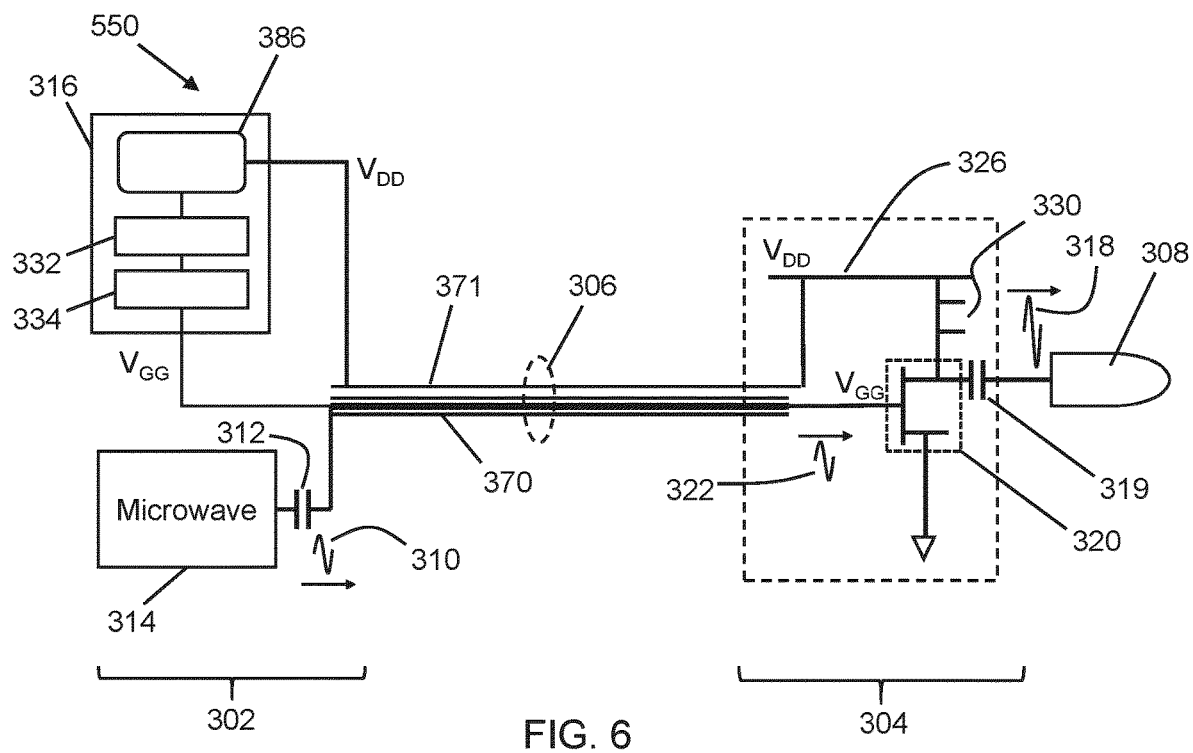
FIG. 6 is a schematic diagram of a distal instrument-based microwave generation module that is another embodiment of the invention.

FIG. 6 is a schematic diagram showing another example of a microwave amplification apparatus 550 that is an embodiment of the invention. Features in common with FIG. 3 are given the same reference number and are not described again.

The apparatus 550 in FIG. 6 differs from that in FIG. 3 in that the gate voltage is generated at the proximal end and transferred as a secondary DC signal through the cable assembly 306. Thus, the DC power generator 316 in this example may include the DC source 386 that outputs the DC signal (having voltage $V_{DD}$) for transport along the cable assembly 306. In this example, the cable assembly includes a dedicated transmission line 371 for the DC signal. In the proximal portion 304, a distal end of the transmission line 371 is coupled to the drain of the power amplifier 320 through a low pass filter 330 that may be of the type described above. The dedicated transmission line 371 may be connected directly to the drain via the low pass filter, or may be connected via voltage rail 326 as shown in FIG. 6.

The DC power generator 316 may also include means for generating the bias voltage for the power amplifier. In some examples, the bias voltage may be generated using a separate DC source, e.g. operating at a lower voltage than the DC source 386 for the drain voltage. In the embodiment shown in FIG. 6, however, the bias voltage is obtained from the same DC source as the drain voltage by providing a gate voltage extraction module 332 in the proximal portion 302. The gate voltage extraction module 332 may be configured for operation in the same way as described above. The proximal portion 302 may also include a gate control module 334 for controlling the bias voltage that is supplied to the cable assembly 306.

In this example, the bias voltage is conveyed to the distal portion along an inner conductor of a coaxial transmission line 370 in the cable assembly 306. The coaxial transmission line 370 is also used to convey the microwave signal 310 from the microwave signal generator 314.

In some examples, the dedicated line 371 for the DC signal may be an additional conductive layer formed around an outer conductor of the coaxial transmission line 370 and separated therefrom by an insulating layer, e.g. effectively to form a signal triaxial cable. In this example it may be desirable to include a low filter in the distal portion 304 at the point where the DC signal is separated from the coaxial transmission line 370 to avoid the microwave signal from leaking on to the voltage rail 326.

The invention claimed is:

1. A microwave amplification apparatus for an electrosurgical instrument, the microwave amplification apparatus comprising:
 a cable assembly;
 a proximal launch portion connected to a proximal end of the cable assembly, the proximal launch portion comprising:
  a DC source configured to launch a DC signal along the cable assembly; and
  a microwave source configured to launch a microwave signal along the cable assembly;
 a distal amplification portion connected to a distal end of the cable assembly, the distal amplification portion comprising a power amplifier configured to receive the microwave signal as an input signal to be amplified,
 wherein the distal amplification portion is configured to apply the DC signal as a drain voltage across the power amplifier; and
 a gate voltage extraction module configured to extract a bias voltage from the DC signal and apply it to a gate of the power amplifier;

wherein the power amplifier has an output that is connectable to deliver an amplified microwave signal to a structure that is configured to deliver microwave energy into biological tissue; and wherein the gate voltage extraction module is configured to extract a pair of bias voltages from the DC signal, wherein the pair of bias voltages comprises a first bias voltage corresponding to a non-conducting state of the power amplifier, and a second bias voltage corresponding to a conducting state of the power amplifier.

2. The microwave amplification apparatus of claim 1, wherein the gate voltage extraction module comprises a DC-DC converter configured to down convert a voltage of the DC signal to generate the bias voltage.

3. The microwave amplification apparatus of claim 2, wherein the DC-DC converter comprises a buck converter.

4. The microwave amplification apparatus of claim 1, wherein the gate voltage extraction module comprises a pair of buck converters connected in parallel, wherein the pair of buck converters comprises a first buck converter for generating the first bias voltage, and a second buck converter for generating the second bias voltage.

5. The microwave amplification apparatus of claim 1 further comprising a gate control module configured to selectively apply the first bias voltage or the second bias voltage to the gate of the power amplifier.

6. The microwave amplification apparatus of claim 5, wherein the gate control module comprises a switch arranged to selectively apply the first bias voltage or the second bias voltage to the gate of the power amplifier.

7. The microwave amplification apparatus of claim 6, wherein the distal amplification portion comprises a voltage rail arranged to adopt an operational voltage provided by the DC signal, and wherein the switch is configured to select the second bias voltage upon application of the operational voltage to the voltage rail.

8. The microwave amplification apparatus of claim 1, wherein the gate control module further comprises a delay circuit arranged to introduce a time lag between application of the operational voltage to the voltage rail and actuation of the switch to select the second bias voltage.

9. The microwave amplification apparatus of claim 1, wherein the first bias voltage and the second bias voltage both have a polarity that is opposite to the drain voltage.

10. The microwave amplification apparatus of claim 1, wherein the gate voltage extraction module is in the distal amplification portion.

11. The microwave amplification apparatus of claim 10 further comprising a low pass filter connected between the gate voltage extraction module and the gate of the power amplifier.

12. The microwave amplification apparatus of claim 11, wherein the low pass filter comprises a pair of quarter wave stubs that each have a length of $$\frac{(2n-1)\lambda}{4},$$

wherein the pair of quarter wave stubs comprises a first quarter wave stub located at a distance $$\frac{n\lambda}{2}$$

from the gate of the power amplifier, and a second quarter wave stub spaced from the first quarter wave stub by a distance $$\frac{n\lambda}{2},$$

where λ is a wavelength of the microwave signal, and n is a whole number equal to 1 or more.

13. The microwave amplification apparatus of claim 1, wherein the gate voltage extraction module is in the proximal launch portion, and wherein the DC signal includes a bias voltage conveyed by the cable assembly to the distal amplification portion.

14. The microwave amplification apparatus of claim 1, wherein the cable assembly comprises a coaxial transmission line that comprises an inner conductor separated from an outer conductor by a dielectric material, wherein the microwave signal is conveyed by the coaxial transmission line, and wherein the DC signal is conveyed along the inner conductor.

15. The microwave amplification apparatus of claim 14, wherein the microwave signal is coupled into the coaxial transmission line via a capacitor.

16. The microwave amplification apparatus of claim 1, wherein the output of the power amplifier includes a capacitor configured to couple the amplified microwave signal to the structure.

17. The microwave amplification apparatus of claim 1, wherein the microwave source is further configured to launch the microwave signal having a power equal to or less than 10 W at the proximal end of the cable assembly.

18. The microwave amplification apparatus of claim 1, wherein the distal amplification portion comprises a voltage rail arranged to adopt an operational voltage provided by the DC signal, wherein the voltage rail is connected to a distal end of the cable assembly by a first connection line to receive the DC signal, wherein the voltage rail is connected to a drain of the power amplifier by a second connection line to provide the drain voltage.

19. The microwave amplification apparatus of claim 18 further comprising a proximal low pass filter on the first connection line and a distal low pass filter on the second connection line.

20. The microwave amplification apparatus of claim 19, wherein the proximal low pass filter comprises a pair of quarter wave stubs that each have a length of $$\frac{(2n-1)\lambda}{4},$$

wherein the pair of quarter wave stubs comprises a first quarter wave stub located at a distance $$\frac{n\lambda}{2}$$

from a connection point between the first connection line and the cable assembly, and a second quarter wave stub spaced from the first quarter wave stub by a distance $$\frac{n\lambda}{2},$$

where λ is a wavelength of the microwave signal, and n is a whole number equal to 1 or more.

21. The microwave amplification apparatus of claim 19, wherein the distal low pass filter comprises a pair of quarter wave stubs that each have a length of $$\frac{(2n-1)\lambda}{4},$$

wherein the pair of quarter wave stubs comprises a first quarter wave stub located at a distance $$\frac{n\lambda}{2}$$

from the drain of the power amplifier, and a second quarter wave stub spaced from the first quarter wave stub by a distance $$\frac{n\lambda}{2},$$

where λ is a wavelength of the microwave signal, and n is a whole number equal to 1 or more.

22. An electrosurgical instrument comprising:
a microwave amplification apparatus according to claim 1; and
a radiating tip connected to the output of the power amplifier, wherein the radiating tip comprises an antenna configured to radiate the amplified microwave signal into biological tissue.

23. The electrosurgical instrument of claim 22, wherein the microwave amplification apparatus and radiating tip are dimensioned to be insertable through an instrument channel of a surgical scoping device.

\* \* \* \* \*